US011046722B2

(12) United States Patent
Vergés Milano et al.

(10) Patent No.: US 11,046,722 B2
(45) Date of Patent: Jun. 29, 2021

(54) SULPHATED DISACCHARIDES FOR THE TREATMENT OF NEUROPATHIC PAIN

(71) Applicants: BIOIBERICA, S.A.U., Palafolls (ES); UNIVERSIDAD AUTONOMA DE MADRID, Madrid (ES); FUNDACIÓN TEÓFILO HERNANDO, Madrid (ES)

(72) Inventors: Josep Vergés Milano, Barcelona (ES); Eulàlia Montell Bonaventura, Sant Quirze del Vallès (ES); Ramon Ruhí Roura, Barcelona (ES); Carlos Raúl Aláez Versón, Blanes (ES); Antonio García García, Alpedrete (ES); Manuela García López, Madrid (ES); Juan Fernando Padín Nogueira, Marín (ES); Marcos Maroto Pérez, Madrid (ES); Javier Egea Máiquez, Madrid (ES)

(73) Assignees: BIOBERICA, S.A.U., Palafolls (ES); UNIVERSIDAD AUTONOMA DE MADRID, Madrid (ES); FUNDACION TEOFILO HERNANDO, Madrid (ES)

( * ) Notice: Subject to any disclaimer, the term of this patent is extended or adjusted under 35 U.S.C. 154(b) by 0 days.

(21) Appl. No.: 16/499,600

(22) PCT Filed: Mar. 6, 2018

(86) PCT No.: PCT/EP2018/055430
§ 371 (c)(1),
(2) Date: Sep. 30, 2019

(87) PCT Pub. No.: WO2018/177693
PCT Pub. Date: Oct. 4, 2018

(65) Prior Publication Data
US 2020/0102339 A1    Apr. 2, 2020

(30) Foreign Application Priority Data
Mar. 29, 2017    (ES) ................ ES201730458

(51) Int. Cl.
*C07H 11/00* (2006.01)
*A61P 25/02* (2006.01)

(52) U.S. Cl.
CPC .............. *C07H 11/00* (2013.01); *A61P 25/02* (2018.01)

(58) Field of Classification Search
CPC ................................ C07H 11/00; A61P 25/02
USPC ........................................................ 514/53
See application file for complete search history.

(56) References Cited

FOREIGN PATENT DOCUMENTS

| EP | 1300411 A1 | 4/2003 |
| WO | 2005118609 A2 | 12/2005 |
| WO | 2008151898 A1 | 12/2008 |
| WO | 2011080203 A1 | 7/2011 |

OTHER PUBLICATIONS

Foley et al. (PAIN® 154 (2013) 632-642).*
Harald Breivik, "Survey of Chronic Pain in Europe: Prevalence, Impact on Daily Life, and Treatment" Journal, 2006, 287-333, European Journal of Pain, Science Direct.
R.D. Treede, "Neuropathic Pain: Redefinition and a Grading System for Clinical and Research Purposes" Article, 2008, 1630-1636, vol. 70, Neurology, AAN Enterprises, Inc.
T. Dimitroulas, "Neuropathic Pain in Osteoarthritis: a Review of Pathophysiological Mechanisms and Implications for Treatment", Journal, 2014, 145-154, vol. 44, No. 2, Seminars in Arthritis and Rheumatism.
Angel Oteo-Alvaro, "High Prevalence of Neuropathic Pain Features in Patients with Knee Osteoarthritis: A Cross-Sectional Study", Journal, 2015, 618-626, vol. 15, No. 7, PAIN Practice.
Sukhleen K. Momi, "Neuropathic Pain as Part of Chronic Widespread Pain: Environmental and Genetic Influences", Research Paper, 2015, 2100-2106, vol. 156, No. 10, PAIN, International Association for the Study of Pain.
A.W. Christensen, "Non-Nociceptive Pain in Rheumatoid Arthritis is Frequent and Affects Disease Activity Estimation: Cross-Section Data from the FRAME Study", Journal, 2016, 1-9, Scandinavian Journal of Rheumatology.
Jana Koroschetz, "Fibromyalgia and Neuropathic Pain—Differences and Similarities. A Comparison of 3057 Patients with Diabetic Painful Neuropathy and Fibromyalgia", 2011, 1-8, vol. 11, BMC Neurology.
David L. H. Bennett, "Informed Drug Choices for Neuropathic Pain", Journal, 2015, 129-130, vol. 14, Neurology.
Ian Gilron, "Neuropathic Pain: Principles of Diagnosis and Treatment", 2015, 532-545, Symposium of Pain Medicine, Mayo Clinic.
Kinga Salat, "New Investigational Drugs for the Treatment of Neuropathic Pain", 2014, 1-12, vol. 23, No. 8, Drugs, Expert Opinion.
Jose M. Entrena, "Antagonism by Haloperidol and its Metabolites of Mechanical Hypersensitivity Induced by Intraplantar Capsaicin in Mice: Role of Sigma-1 Receptors", Journal, 2009, 21-33, vol. 205, Psychopharmacology, Springer.
Isabelle Decosterd, "Spared Nerve Injury: an Animal Model of Persistent Peripheral Neuropathic Pain", Journal, 2000, 149-158, vol. 87, PAIN, International Association for the Study of Pain.

(Continued)

*Primary Examiner* — Shaojia A Jiang
*Assistant Examiner* — Michael C Henry
(74) *Attorney, Agent, or Firm* — Hayes Soloway PC

(57) ABSTRACT

The present invention relates to sulphated disaccharides of formula (I) for use in the treatment of neuropathic pain. The present invention also relates to a pharmaceutical composition comprising the compound of formula (I) and at least one pharmaceutically acceptable excipient for use in the treatment of neuropathic pain. The compounds of formula (I) were effective in several experimental models of neuropathic pain for which reason these compounds can be used effectively for the treatment of different types of neuropathic pain and the clinical manifestations thereof, for example, mechanical allodynia or cold allodynia.

17 Claims, 4 Drawing Sheets

(56) References Cited

OTHER PUBLICATIONS

Shad B. Smith, "Paclitaxel-Induced Neuropathic Hypersensitivity in Mice: Responses in 10 Inbred Mouse Strains", 2004, 2593-2604, vol. 74, Life Sciences, Science Direct.

Rosemary C. Polomano, "Chemotherapy-Evoked Painful Peripheral Neuropathy", Journal, 2001, 8-14, vol. 2, No. 1, Pain Medicine, Blackwell Science, Inc.

Yoon Choi, "Behavior Signs of Ongoing Pain and Cold Allodynia in a Rat Model of Neuropathic Pain", Journal, 1994, 369-376, vol. 59, PAIN, Elsevier Science B.V.

C. Courteix, "Streptozocin-Induced Diabetic Rats: Behavioural Evidence for a Model of Chronic Pain", Journal, 1993, 81-88, vol. 53, PAIN, Elsevier Science Publishers B.V.

Lippincott Williams and Wilkins, "Remington: The Science and Practice of Pharmacy", Book, 2005, 21st Edition, [ISBN 0-683-306472].

Raymond C. Rowe, "Handbook of Pharmaceutical Excipients", Book, 2009, 6th Edition, Pharmaceutical Press, [ISBN 978-0-85369-792-3].

J. Egea, "Small Synthetic Hyaluronan Disaccharides Afford Neuroprotection in Brain Ischemia-Related Models", 2014, 313-322, vol. 265, Neuroscience.

Shu-Ping Jiang, "Celecoxib Reverts Oxaliplatin-Induced Neuropathic Pain Through Inhibiting PI3K/Akt2 Pathway in the Mouse Dorsal Root Ganglion", Research Paper, Nov. 9, 2015, 11-16, vol. 275, Experimental Neurology, Elsevier.

\* cited by examiner

SULPHATED DISACCHARIDES FOR THE TREATMENT OF NEUROPATHIC PAIN

CROSS-REFERENCE TO RELATED APPLICATIONS AND PRIORITY

This patent application claims priority from PCT Patent Application No. PCT/EP2018/055430 filed Mar. 6, 2018, which claims priority from ES Patent Application No. P201730458 filed Mar. 29, 2017. Each of these patent applications are herein incorporated by reference in its/their entirety.

APPLICATION FIELD

The present invention relates to pharmacotherapy of pain, and particularly, neuropathic-type pain.

STATE OF THE ART

Pain is considered one of the main current public health problems, due to the significant socioeconomic impact linked to this pathology. Several studies have shown that chronic pain, from moderate to high intensity, affects approximately 20% of the adult population in Europe and notably impairs the quality of life of patients; these studies also showed that an elevated proportion of patients perceive that the current treatments do not provide adequate pain management, as described for example in the article by Breivik et al., *Survey of chronic pain in Europe: Prevalence, impact on daily life and treatment*, Eur. J. Pain, 2006, 10, 287-333.

Commonly, two types of pain are clinically relevant namely, nociceptive pain and neuropathic pain. Nociceptive pain is usually caused by an injury or damage to a tissue, which in turn triggers a stimulus for pain receptors' activation, generally for a short time; this can be considered an alarm and defense system, which enables the presence of damage in the organism to be detected.

In contrast, neuropathic pain has its origin in an incorrect functioning of the nociceptive pathways that transmit the information related to pain perception, and is defined as the pain originated as a direct consequence of an injury or disease that affects the somatosensory system (Treede et al., *Neuropathic pain: redefinition and a grading system for clinical and research purposes*, Neurology, 2008, 70, 1630-5).

According to its anatomical source, neuropathic pain can be classified as peripheral neuropathic pain, when it is due to an injury or dysfunction of the peripheral nervous system, and central neuropathic pain, when its origin is an injury or dysfunction of the central nervous system.

Neuropathic pain is usually also classified according to its ethiology; this comprises post-herpetic neuralgia, diabetic neuropathy, HIV-related neuropathy, post-chemotherapy neuropathy, trigeminal neuralgia, post-surgical neuralgia, post-stroke pain, pain from multiple sclerosis, pain from spinal cord injuries, or pain related to the phantom limb, among others.

Furthermore, some studies available in the state of the art concluded that pathologies such as rheumatoid arthritis or osteoarthritis, traditionally only associated with nociceptive pain of inflammatory origin, often cause pain of neuropathic origin, as described in the articles by Dimitroulas et al., *Neuropathic pain in osteoarthritis: a review of pathophysiological mechanisms and implications for treatment*, Semin. Arthritis. Rheum., 2014, 44 (2), 145-54; and Christensen et al., *Non-nociceptive pain in rheumatoid arthritis is frequent and affects disease activity estimation: cross-sectional data from the FRAME study*, Scand. J. Rheumatol., 2016 (DOI: 10.3109/03009742.2016.1139174). This proportion of patients with osteoarthritis that have neuropathic pain reaches 50% in patients who had undergone knee surgery or had gone to rehabilitation, indicating a correlation between the development of the disease and the appearance of neuropathic pain, as described in the article by Oteo-Alvaro et al., *High prevalence of neuropathic pain features in patients with knee osteoarthritis: A cross-sectional study*, Pain Pract., 2015, 15 (7), 618-26.

Likewise, within the different manifestations of fibromyalgia, the presence of neuropathic-type pain was detected, and some studies demonstrate the existence of common factors, which can be sensory perceptions, between patients with neuropathic pain and those with fibromyalgia, as described, for example, in the article by Momi et al., *Neuropathic pain as part of chronic widespread pain: environmental and genetic influences*, Pain, 2015, 156 (10), 2100-6, or in Koroschetz et al., *Fibromyalgia and neuropathic pain—differences and similarities. A comparison of 3057 patients with diabetic painful neuropathy and fibromyalgia*, BMC Neurol., 2011, 11:55. For this reason fibromyalgia is treated with the same medicinal products that are used to treat neuropathic pain. In fact, the first medicinal product specifically approved to treat fibromyalgia in the U.S. was Lyrica® (pregabalin) in 2007, three years after obtaining the marketing authorization for the treatment indication of neuropathic pain associated with peripheral diabetic neuropathy or post-herpetic neuropathic pain.

Recent studies indicate that neuropathic pain affects 7-8% of the population, and it is estimated that this proportion could increase in the future, among other factors, due to increasing incidence of diabetes, and the improved rate of survival from cancer, as described, for example in the article by Bennett D. L., *Informed drug choices for neuropathic pain*, Lancet Neurol., 2015, 14, 129-30.

First-line treatments for neuropathic pain include some anticonvulsants such as gabapentin and pregabalin; tricyclic antidepressants, such as amitriptyline, imipramine or clomipramine; or serotonin-norepinephrine reuptake inhibitors such as duloxetine and venlafaxine. However, these drugs only provide modest effectiveness in treating neuropathic pain, which is very variable depending on the type of specific pain (Gilron et al., *Neuropathic pain: principles of diagnosis and treatment*, MayoClin. Proc., 2015, 90, 532-545).

Numerous publications of the state of the art coincide in considering that the therapeutic arsenal currently available for treating neuropathic pain is reduced and has limited effectiveness; therefore, there is a need to develop new alternatives, as highlighted in the article by Salat et al., *New investigational drugs for the treatment of neuropathic pain*, Expert Opin. Investig. Drugs, 2014, 23, 1093-104, in which a few of the new compounds currently in development for treating neuropathic pain are reviewed, such as, for example, a few selective inhibitors of voltage-gated sodium $Na_v1.7$-type channels, such as raxatrigine (CNV1014802), funapide (XEN402) or PF-05089771; N or T-type calcium channel antagonists, such as Z160 or Z944; angiotensin II $AT_2$ receptor inhibitors, such as EMA401; or nerve-growth factor (NGF) inhibitors, for example, tanezumab.

Thus, in the light of the high prevalence of neuropathic pain, its profound impact on the quality of life of patients, and the limited effectiveness of current treatments, the need of new drugs that are effective for treating neuropathic pain is an unmet goal; these new drugs will considerably contribute to increase the available therapeutic arsenal and enable a better control of neuropathic pain.

OBJECT OF THE INVENTION

The object of the present invention is a sulphated disaccharide of formula (I) for use in the treatment of neuropathic pain.

Another aspect of the invention is a pharmaceutical composition comprising a disaccharide of formula (I) and at least one pharmaceutically acceptable excipient for use in the treatment of neuropathic pain.

DETAILED DESCRIPTION OF THE INVENTION

Figure 1:
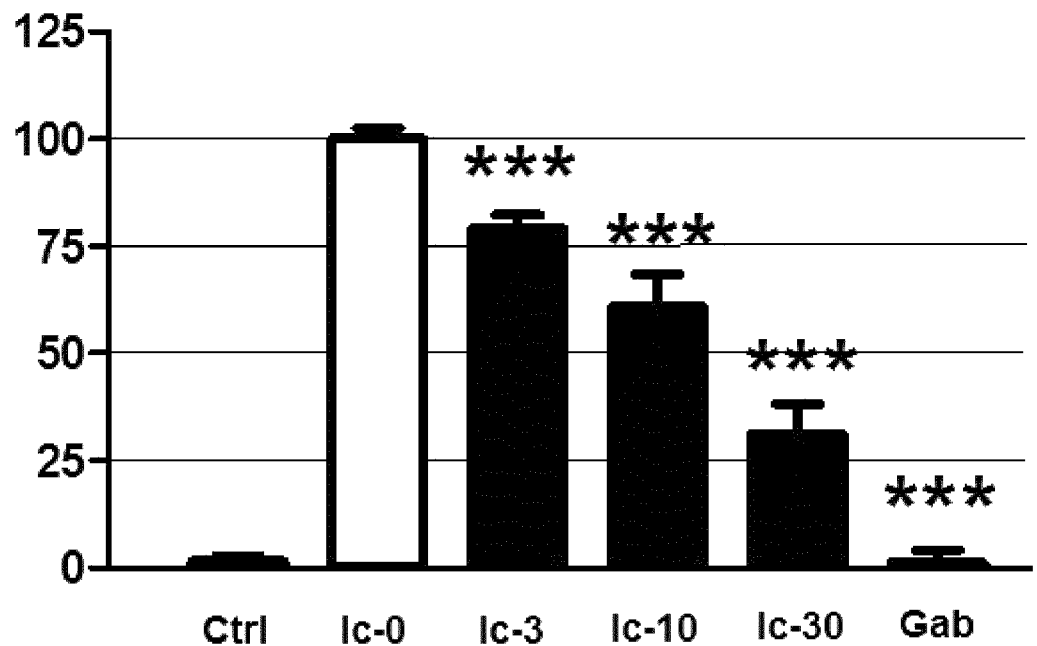
FIG. 1 is a bar graph in which the results obtained with the Ic compound and with gabapentin are shown in an experimental model of mechanical allodynia induced in mice by intraplantar capsaicin injection (Example 1). The Y-axis shows the percentage of allodynia and the X-axis the different treatments. The first bar corresponds to the control group (Ctrl), that is, mice without treatment and without allodynia induction. The second bar (Ic-0) corresponds to animals with allodynia induced by capsaicin injection, and without pharmacological treatment. The rest of the bars correspond to animals with allodynia induced by capsaicin injection subjected to different oral treatments with compound Ic namely: 3 mg/Kg (Ic-3), 10 mg/Kg (Ic-10), 30 mg/Kg (Ic-30), and 40 mg/Kg gabapentin (Gab). The data points are means±SEM of at least 10 animals per experimental group (' $p<0.001$ ANOVA and Dunnett's test), with respect to Ic-0.

The object of the present invention is a compound of formula (I):

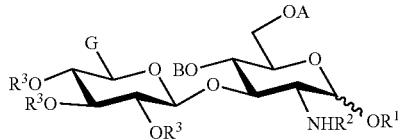

wherein:
- $R^1$ is selected from among hydrogen, linear or branched $C_1$-$C_4$ alkyl, phenylalkyl of less than 10 carbon atoms and —$COCH_3$;
- $R^2$ is selected from among hydrogen, —$COCH_3$ and —$SO_3Y$;
- $R^3$ is selected from among hydrogen, linear or branched $C_1$-$C_4$ alkyl, phenylalkyl of less than 10 carbon atoms, —$COCH_3$ and —COPh, where Ph is phenyl;
- G is selected from among —$COOR^4$ and —COOY;
- A and B are selected, independently from each other, from among hydrogen, —$SO_3H$, —$SO_3Y$ and —$COCH_3$;
wherein necessarily either A or B is either —$SO_3H$, or —$SO_3Y$,
- $R^4$ is selected from among hydrogen, $C_1$-$C_2$ alkyl and arylalkyl of less than 16 carbon atoms, and
- Y is an organic or inorganic cation;

or a pharmaceutically acceptable salt or solvate thereof, for use in the treatment of neuropathic pain.

Alternatively, the object of the present invention can be formulated as the use of a compound of formula (I), or even a pharmaceutically acceptable salt or solvate thereof, for the manufacture of a medicament for the treatment of neuropathic pain.

Or alternatively, the object of the present invention can also be formulated as a method for treating neuropathic pain in a subject in need thereof, comprising administrating of a compound of formula (I), or even a pharmaceutically acceptable salt or solvate thereof. Typically, a therapeutically effective amount of the compound of formula (I) is administered.

The disaccharides represented by formula (I) had been previously described in the state of the art in relation to treating osteoarthritis, or diseases or injuries related to tendons, ligaments or bones, and also by the neuroprotective activity thereof due to inhibition of the production of reactive oxygen species.

The authors of the present invention have noted that, surprisingly, the disaccharides of formula (I) are notably effective for treating neuropathic pain, as was demonstrated in a series of models that are experimental, specific and entirely representative for such pathology.

Compound of Formula (I)

The compound of formula (I) is a disaccharide with β bonds (1→3) between glucuronic acid, or a derivative thereof, and a derivative of glucosamine, and it has at least one sulphate group in the C-4 and/or C-6 position of the glucosamine ring.

The disaccharides of formula (I) are described in the patent document EP1300411-A1, in which methods for the preparation thereof are provided. In such document, the disaccharides of formula (I) are proposed as an alternative to the use of hyaluronic acid for treating osteoarthritis and inflammation.

Additionally, the use of the disaccharides of formula (I) for treating tendon, ligament or bone diseases or injuries has also been described, as described in international patent application WO2008/151898-A1, as well as the use thereof as neuroprotective medicines and in treating neurodegenerative and/or neurovascular diseases, due to the capacity thereof for reducing the formation of reactive oxygen species, protecting from cellular death induced by oxidative stress and by oxygen and glucose deprivation, as described in international patent application WO2011/080203-A1. In this latter document an alternative method for preparing the compounds of formula (I) is also provided.

In the definition of the compound of formula (I), a linear or branched $C_1$-$C_4$ alkyl group includes, as is well-known in the art, the following alkyl groups: methyl, ethyl, n-propyl, isopropyl, n-butyl, isobutyl, sec-butyl and tert-butyl; a $C_1$-$C_2$ alkyl group includes the methyl and ethyl groups; a phenylalkyl group of less than 10 carbon atoms refers to an -alk-Ph group wherein alk represents a linear or branched alkylene group and Ph represents a phenyl group, wherein the total number of carbon atoms of the -alk-Ph group is less than 10; an arylalkyl group of less than 16 carbon atoms refers to an -alk-Ar group wherein alk represents a linear or branched alkylene group, and Ar represents an aromatic, monocyclic or polycyclic carbocycle, not substituted, and wherein the total number of carbon atoms of the -alk-Ar group is less than 16; Y is an organic or inorganic cation, in other words, Y is chosen between an inorganic cation, for example an alkaline metal, typically lithium, sodium or potassium, and an organic cation, for example, an ammonium group or an alkylammonium group.

The compound of formula (I) has an anomeric carbon in the structure thereof, which is represented with the wavy link in the figure. The use according to the present invention includes the compound of formula (I) in the two anomeric forms thereof, α and δ, as well as the mixtures thereof.

In a preferred embodiment, the use according to the present invention relates to a compound of formula (I), according to what was defined previously, wherein:
- $R^1$ is selected from among hydrogen and linear $C_1$-$C_4$ alkyl, and
- G is selected from among —$COOR^4$ and —COOY, wherein $R^4$ is hydrogen or $C_1$-$C_2$ alkyl and Y is an inorganic cation, preferably the sodium cation.

In a more preferred embodiment the compound of formula (I) is that wherein $R^1$ is hydrogen, $R^2$ is —$COCH_3$ and $R^3$ is hydrogen. In another equally preferred embodiment, $R^1$ is methyl, $R^2$ is —COCH$_3$ and $R^3$ is hydrogen.

In a particularly preferred embodiment the compound of formula (I) is that wherein A is hydrogen, B is —SO$_3$Y and G is —COOY, wherein Y is an inorganic cation, preferably sodium. In another equally preferred embodiment, A is —SO$_3$Y, B is hydrogen and G is —COOY, wherein Y is an inorganic cation, preferably sodium. In another equally preferred embodiment A and B are —SO$_3$Y and G is —COOY, wherein Y is an inorganic cation, preferably sodium.

In an even more preferred embodiment of the use according to the present invention, the compound of formula (I) is chosen from among the group made up of the following compounds:

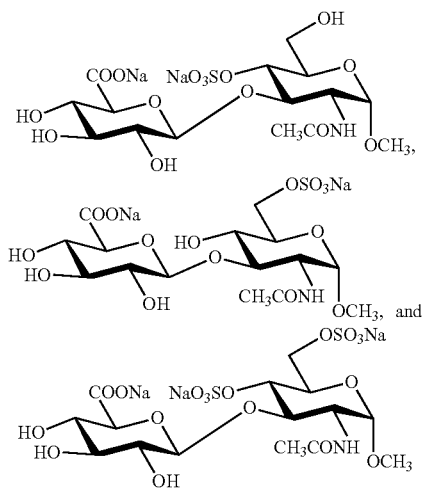

In a particularly preferred embodiment of the use according to the present invention the compound of formula (I) is the following:

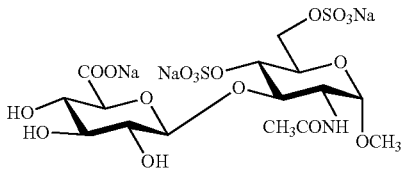

This compound (methyl 2-acetamido-2-desoxi-3-O-(β-D-glucopyranosyl uronic acid)-4,6-di-O-sulfo-α-D-glucopyranoside trisodium salt), is called compound Ic in the examples.

Treatment of Neuropathic Pain

Neuropathic pain refers to, as it is well known by a person skilled in the art, pain that originates from a dysfunction of the nervous system, as a direct consequence of an injury or disease that affects the somatosensory system.

The types of neuropathic pain susceptible to being treated with compounds of formula (I), according to the use of the present invention are, for example, diabetic neuropathy, postherpetic neuralgia, neuropathy induced by chemotherapy, HIV-related neuropathy, rheumatoid arthritis-related neuropathy, osteoarthritis-related neuropathy, fibromyalgia-related neuropathy, several craniofacial neuralgias, such as trigeminal neuralgia, glossopharyngeal neuralgia, sphenopalatine ganglion neuralgia, vidian nerve neuralgia, persistent idiopathic facial pain or primary atypical facial neuralgia, for example; pain related to phantom limbs, cerebral vascular post-accident pain, pain from multiple sclerosis or pain from spinal cord injuries, among others.

The most common symptoms of neuropathic pain are persistent sharp, searing, stinging or burning pain, with lancinating crisis, dysesthesias and paresthesias. Among the most characteristic clinical manifestations of neuropathic pain are allodynia and hyperalgesia, both related to a hypersensitivity when exposed to external stimuli. Allodynia relates to the perception of stimuli that normally do not cause pain as painful, while hyperalgesia is defined as an increased response to a modestly painful stimulus. Usually a difference is made between thermal allodynia (hot or cold) and mechanical allodynia. Cold allodynia, for example, is characterized by an exaggerated sensitivity to cold that leads to experiencing pain at temperatures that, in normal conditions are perceived as harmlessly cool.

The effectiveness of the compounds of formula (I) was tested, in particular of compound Ic, for treating neuropathic pain, by using several experimental models representative of such pathology. Surprisingly, it was observed that compound Ic is notably effective in treating and/or preventing the symptoms of neuropathic pain in all models tested.

Thus, in Example 1, an experimental trial is described performed on mice with mechanical allodynia induced by intraplantar capsaicin injection, according to the model described in the article by Entrena et al., *Antagonism by haloperidol and its metabolites of mechanical hypersensitivity induced by intraplantar capsaicin in mice: role of sigma-1 receptors*, Psychopharmacology, 2009, 205, 21-33. This trial is based on hypersensitivity induced in the mice by means of injecting capsaicin in the right hind paw. The allodynia is quantified by measuring the decrease in latency time in the hypersensitized mice until paw withdrawal, when a mechanical stimulus is applied to it. As described in such example, compound Ic shows a notable effect in the reversion of the allodynia in this model (FIG. 1).

Figure 2:
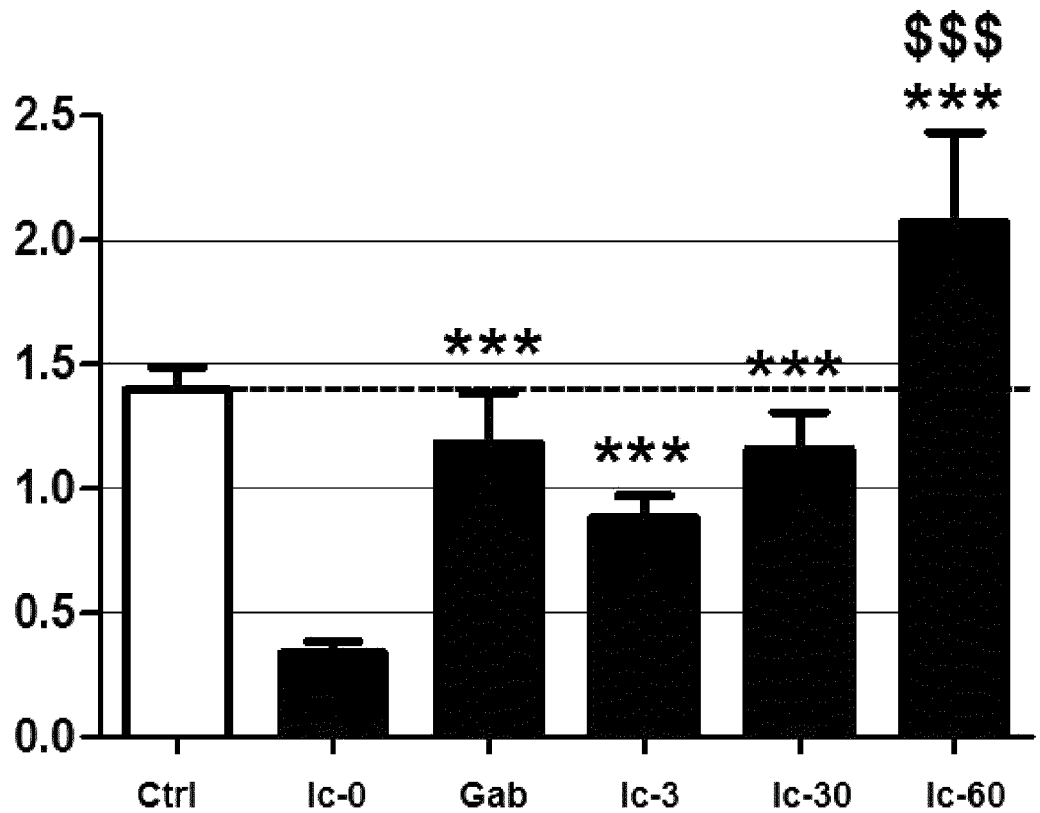
FIG. 2 is a bar graph in which the results obtained with compound Ic and gabapentin are shown in an experimental model of mechanical allodynia induced in mice after chronic ligation of the sciatic nerve (Example 2). On the Y-axis half of the threshold force that is necessary to apply in order to cause paw withdrawal is shown (50% pain threshold, in grams, g) and on the X-axis the different groups and treatments carried out are shown in bars. The first bar (Ctrl) corresponds to the control group of animals without allodynia, that are not subjected to surgery, and without any treatment. The second bar (Ic-0) corresponds to animals with allodynia induced by ligation of the sciatic nerve, without pharmacological treatment. The rest of the bars correspond to animals with allodynia induced by ligation of the sciatic nerve, subjected to different oral treatments: namely 40 mg/Kg gabapentin (Gab) and increasing doses of compound Ic i.e., 3 mg/Kg (Ic-3), 30 mg/Kg (Ic-30), and 60 mg/Kg (Ic-60). The data points are means±SEM of at least 6 animals per experimental group (*** $p<0.001$ compared to the Ic-0 group; \$\$\$ $p<0.001$ compared to the control group; one-way ANOVA followed by Tukey's post-hoc test).

In Example 2, an experimental trial on mechanical allodynia induced in mice by chronic ligation of the sciatic nerve is described, according to the model described in the article by Decosterd et al., *Spared nerve injury: an animal model of persistent peripheral neuropathic pain*, Pain, 2000, 149-158. This model is based on causing mechanical allodynia in mice by means of ligation of two of the three branches of the sciatic nerve (tibial and peroneal), leaving the sural branch intact. The allodynia induced in this manner is quantified by the reduction observed in the threshold force that is necessary to apply in order to produce animal's paw withdrawal in those subjected to the ligation. As described in such example, it is observed that the administration of different doses of compound Ic is effective in reversing the allodynia induced in this model (FIGS. 1 and 2).

In Example 3 an experimental model is used in mice based on inducing allodynia by intraperitoneal injection of paclitaxel, as described in the articles by Smith et al., *Paclitaxel-induced neuropathic hypersensitivity in mice: responses in 10 inbred mouse strains*, Life Sci., 2014, 2593-2604 and Palomano et al., *Chemotherapy-evoked painful peripheral neuropathy*, Pain Med., 2001, 2 (1), 8-14. In alternative trials, compound Ic was administered after allodynia induction by paclitaxel, or it was administered jointly with this chemotherapy medication. It is observed that compound Ic is effective at both reversing the allodynia induced by paclitaxel (FIG. 4), and preventing the development thereof when coadministered with paclitaxel (FIG. 5).

Figure 6:
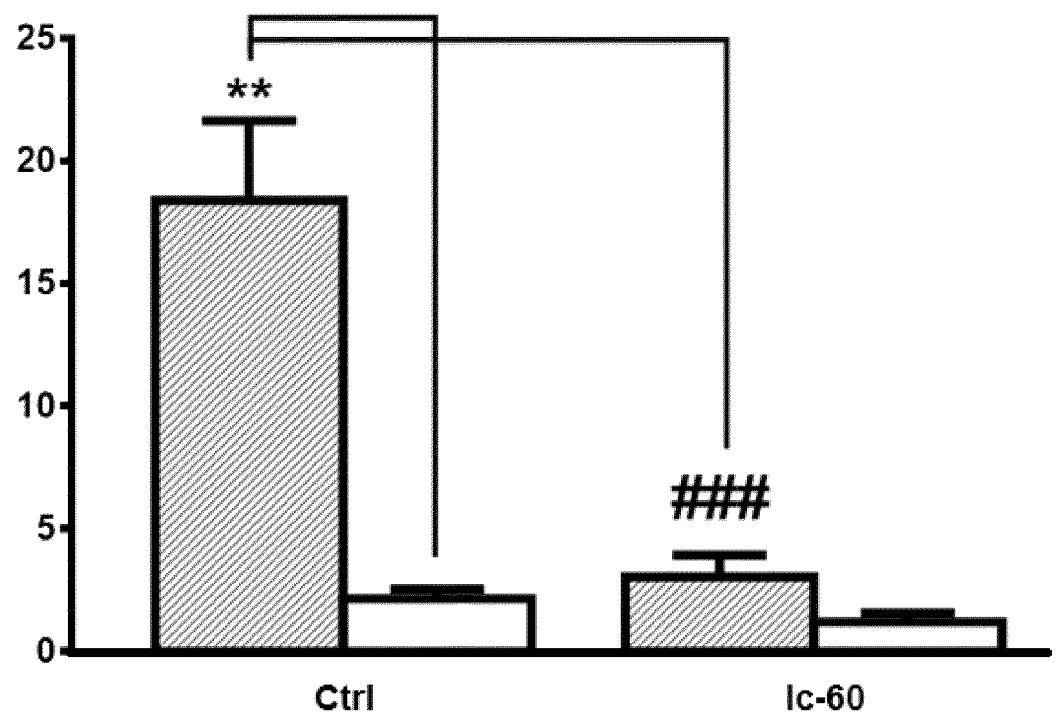
FIG. 6 shows the results obtained with compound Ic in an experimental model in mice with cold allodynia induced by subcutaneous injection of carrageenan (Example 4). The sensitivity to cold was quantified by administering a drop of acetone in the plantar surface of the hind paws and subsequently measuring the time the animals spent licking the paw. On the Y-axis the time spent licking the paw (in seconds) is represented and on the X-axis the different treatments are represented. The first pair of bars corresponds to the control group of animals (Ctrl), without pharmacological treatment, while the second pair of bars corresponds to the group of animals treated with 60 mg/Kg of compound (Ic-60). In each group, the left bar (striped) represents the result of the aforementioned test on the hind paw sensitized with carrageenan (ipsilateral) and the right bar represents the results of the aforementioned test on the unsensitized hind paw (contralateral). The data points are means±SEM of at least 7 animals per experimental group (** $p<0.01$, compared to the white bar of the Ctrl, two-way paired t-test; ### $p<0.001$ compared to the gray bar of the Ctrl, two-way unpaired t-test).

In Example 4 an experimental model is used of cold allodynia induced in mice by subcutaneous carrageenan injection, as described in the article by Choi et al., *Behavioral signs of ongoing pain and cold allodynia in a rat model of neuropathic pain*, Pain, 1994, 59 (3), 369-376. This trial is based on causing cold allodynia in mice by subcutaneous carrageenan injection in the plantar surface of one of the hind paws of the animals, and subsequently measuring the sensitivity to cold by applying acetone on the plantar surface of both hind paws: the ipsilateral (the same one where the carrageenan was injected) and the contralateral (the unsensitized hind paw). The sensitivity to cold is quantified by measuring the time the animals spent licking the paw for 5 minutes after the application of the acetone. As described in such example, compound Ic is effective in reversing the cold allodynia according to this model (FIG. 6).

Figure 7:
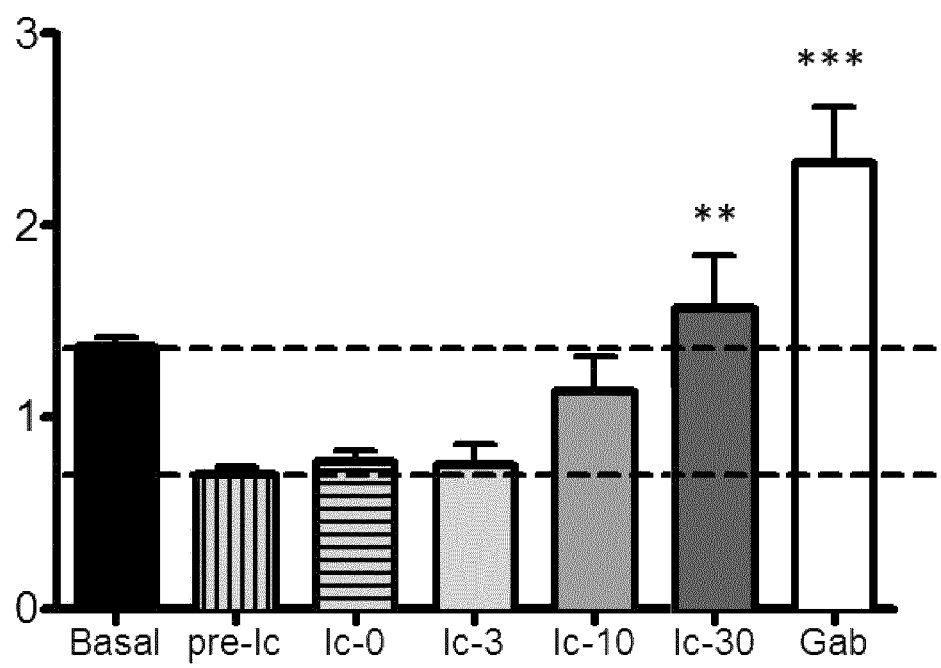
FIG. 7 is a bar graph in which the results obtained with compound Ic are shown in an experimental model in mice with mechanical allodynia due to diabetes induced by injecting streptozotocin (Example 5). On the Y-axis half of the threshold force that is necessary to apply in order to cause paw withdrawal is shown (50% pain threshold, in grams, g) and on the X-axis the different groups and treatments are shown in bars. From left to right, the first bar represents the pain threshold value of the animals before starting the diabetes induced protocol. In the next two bars, the one with vertical lines corresponds with the value at day 25 of the protocol before administering the compound, and the one with horizontal lines to the value of the experimental group after administering saline on the same day of the protocol. Then, the next three bars, in order of increasing gray intensity, represent the values of the 50% threshold force before withdrawing the paw of 3 doses of compound Ic: 3, 10 and 30 mg/kg. Lastly, the white bar shows the value obtained after administering gabapentin, at the dose of 40 mg/kg. In all cases, data points are means±SEM of 7 to 10 animals per experimental group (<0.01. *<0.001 compared to the group of animals given saline; gray bar with horizontal lines. Two-way unpaired t-test).

In Example 5 an experimental trial is described of mechanical allodynia in diabetic mice induced by intraperitoneal streptozotocin injection, based on the model described in the article by Courteix et al., *Streptozotocin-induced diabetic rats: behavioural evidence for a model of chronic pain*, Pain, 1993, 81-88. This model is based on causing a mechanical allodynia in mice by inducing diabetes by means of intraperitoneal streptozotocin injection. It is observed that the administration of different doses of compound Ic is effective in reversing the allodynia induced by diabetes, as quantified by the statistically significant increase observed in the treated animals, of the threshold force that is necessary to apply in order to produce paw withdrawal in the animals (FIG. 7).

The treatment according to the present invention is indicated to be applied to any mammal that needs such treatment, preferably human beings.

Within the framework of the present invention, the term treatment includes the treatment with therapeutic purpose, in other words, aimed at eliminating or reducing the symptoms of neuropathic pain, when these have already been manifested, and also includes treatment with a preventative or prophylactic purpose, in other words, aimed at preventing or delaying the onset of the symptoms of neuropathic pain before they appear, in patients that suffer from diseases or present clinical situations favorable for the development of this pathology, for example, cancer patients subjected to chemotherapy.

In one embodiment, the use according to the present invention specifically relates to reversing or preventing the symptoms of mechanical allodynia or cold allodynia.

In one embodiment, the use according to the present invention relates to treating diabetic neuropathy. Diabetic neuropathy originates as an injury of the peripheral nerves that occurs in diabetic persons, and that is related to the microvascular damage caused by hyperglycemia and the failure of insulin to control the plasma glucose levels.

In another embodiment, the use according to the present invention relates to treating postherpetic neuralgia. Postherpetic neuralgia is a complication associated to shingles, characterized by continuous pain throughout a nerve and the branches thereof, which persists after the herpes outbreak disappears.

In another embodiment, the use according to the present invention relates to treating chemotherapy-induced neuropathy. Peripheral chemotherapy-induced neuropathy is considered the most frequent neurological complication of cancer treatments, and is mainly associated with treatments with the anticancer drugs vincristine, paclitaxel, docetaxel or those that are platinum-based (cisplatin and oxaliplatin), among others.

In another embodiment, the use according to the present invention relates to treating HIV-related neuropathy (human immunodeficiency virus). HIV-related neuropathy is a common complication in HIV patients that has its origin in nerve damage that can be caused both by the virus and by some treatments against HIV, and which generally causes pain, numbness, burning, or itching in the limbs.

In another embodiment, the use according to the present invention relates to treating neuropathy associated with rheumatoid arthritis. This type of neuropathic pain relates to the extraarticular neurological manifestations that some patients with rheumatoid arthritis have, which can involve both the central and peripheral nervous systems.

In another embodiment, the use according to the present invention relates to treating neuropathy associated with osteoarthritis, related to treating the neuropathic-type pain that some patients affected by osteoarthritis manifest.

In another embodiment, the use according to the present invention relates to treating neuropathy associated with fibromyalgia. This use of the invention relates to treating the manifestations of pain of neuropathic origin present in patients with fibromyalgia.

In another embodiment, the use according to the present invention relates to treating trigeminal neuralgia. Trigeminal neuralgia is defined as a neuropathic disorder of the trigeminal nerve that causes sharp pain in parts of the face, and can have its origin in pressure exerted on the trigeminal nerve by a tumor, or by a blood vessel, by trauma or can be associated with multiple sclerosis.

In another embodiment, the use according to the present invention relates to treating glossopharyngeal neuralgia. Glossopharyngeal neuralgia is a neuralgia that affects the glossopharyngeal nerve and is characterized by an intense pain localized around the throat and the ear, and that can be caused by swallowing, chewing, throat clearing or speaking.

In another embodiment, the use according to the present invention relates to treating pain associated with phantom limbs. This type of neuropathic pain relates to the presence of painful sensations in an absent extremity after an amputation.

Pharmaceutical Compositions

Another aspect of the present invention is the use of a pharmaceutical composition comprising a compound of formula (I), as defined previously, or a pharmaceutically acceptable salt or solvate thereof, and at least one pharmaceutically acceptable excipient, for the manufacture of a medicament for the treatment of neuropathic pain.

Or formulated in another way, another aspect of the present invention is a pharmaceutical composition comprising a compound of formula (I), as defined previously, or a pharmaceutically acceptable salt or solvate thereof, and at least one pharmaceutically acceptable excipient, for use in the treatment of neuropathic pain.

Or formulated in another way, another aspect of the invention is a method for treating neuropathic pain in a patient who needs it comprising the administration of a pharmaceutical composition comprising a compound of formula (I), as defined previously, or a pharmaceutically acceptable salt or solvate thereof, and at least one pharmaceutically acceptable excipient.

The pharmaceutical composition, the use of which makes up part of the present invention, can generally be administered by any route of administration; for example, by an oral, sublingual, rectal, nasal or ocular route, by a topical route, or by a parenteral route by means of an injectable form, for example, by an intravenous, subcutaneous, intradermal, intra-articular or intramuscular route.

This composition can be in any dosage form, adapted to the type of administration desired. The common dosage forms and the mode of preparation thereof are well known for the person skilled in the art and are described, for example, in the pharmaceutical technology manual by *Remington, The Science and Practice of Pharmacy*, Lippincott Williams & Wilkins, 21st Edition, 2015, [ISBN 0-683-306472].

In one embodiment of the invention, the pharmaceutical composition is to be administered orally. The dosage forms apt for oral administration can be in liquid form, such as solutions or suspensions, or in solid form, such as pills, capsules, powders or granules, for example.

In another embodiment of the invention, the pharmaceutical composition is to be administered topically. The forms apt for topical administration can be in liquid or semi-solid form, in the form of creams, lotions or pastes, for example.

In another embodiment of the invention, the pharmaceutical composition is to be administered parenterally. The forms apt for parenteral administration can be in the form of solutions, suspensions or emulsions, or in solid form, typically in the form of powders, suitable to be reconstituted with a liquid prior to the administration thereof.

The person skilled in the art will have no difficulty in formulating such composition with the help of pharmaceutically acceptable excipients, chosen according to the type of dosage form and the route of administration. The physical and chemical characteristics of the main excipients, as well as the names of the commercial products under which they are sold can be found, for example, in the book by R. C. Rowe et al., *Handbook of Pharmaceutical Excipients*, Pharmaceutical Press, 6th Edition, 2009, [ISBN 978 0 85369 792 3].

The composition the use that makes up part of the present invention comprises the compound of formula (I), or a pharmaceutically acceptable salt or solvate thereof, typically comprises a therapeutically effective amount of such compound.

That therapeutically effective amount, which is suitable for effectively treating neuropathic pain, can vary based on different factors, such as the route of administration, the specific pathology to be treated and the severity thereof.

Generally, the therapeutically effective daily dose of the compounds of the present invention is comprised between 0.01 mg/Kg/day and 100 mg/Kg/day, more preferably comprised between 1 mg/Kg/day and 30 mg/Kg/day.

Such dose can be administered according to different dosages, adapted to each patient and for each specific pathology, and according to the route of administration and the dosage form used. Typically, a single daily administration can be used, or split into two or more administrations per day. Eventually, treatment regimens with lesser frequencies can be followed, less than one dose per day.

EXAMPLES

The effectiveness of the compounds of formula (I) was tested in several experimental models of neuropathic pain, as described below in Examples 1, 2, 3, 4 and 5. In all cases, the compound chosen as representative of the compounds of formula (I) was the methyl 2-acetamido-2-desoxi-3-O-(β-D-glucopyranosyl uronic acid)-4,6-di-O-sulfo-α-D-glucopyranoside trisodium salt (Ic compound).

Example 1 Effectiveness of the Ic Compound in a Model of Mechanical Allodynia Induced by Capsaicin For this trial, 6 groups of mice were used with between 8 and 12 animals in each group. After leaving an acclimatization time for the animals in the experimentation chambers, a solution with 1 μg of capsaicin, or only solvent (phosphate-buffered saline, PBS) for the control group, was administered in the hind right paw. 15 minutes after the injection, different mechanical stimuli were applied with a von Frey filament with a force of 0.5 g in an esthesiometer, and the values of the latency time until paw withdrawal were recorded. The maximum application time of the mechanical stimulus was 50 seconds and each stimulus was applied 3 times, leaving a minimum interval of 30 seconds between each application, such that the average of the three measurements was the value assigned for each animal for the latency time until withdrawal.

In order to evaluate the effect of compound Ic in allodynia induced in this manner, the compound was administered by gavage dissolved in saline solution, 45 minutes before the trial, in different doses (3, 10 y 30 mg/Kg). For comparative purposes, a group of animals was only treated with the vehicle (saline solution) and another group was treated with gabapentin at a dose of 40 mg/Kg, as a positive control.

In order to quantify the anti-allodynic effect, a value of 100% allodynia was assigned to the latency time of the animals injected with capsaicin and without pharmacological treatment (only treated with the vehicle). The rest of the values were normalized with respect to that one.

The results obtained are represented in the bar graph of FIG. 1, where on the Y-axis the allodynia percentage is represented, and on the X-axis the different groups and treatments carried out are represented: the first bar (Ctrl) represents the control which corresponds to mice without treatment and in which allodynia was not induced, injected only with the phosphate-buffered saline; the second bar (Ic-0) represents the animals with 100% allodynia, in other words, injected with capsaicin, and without treatment with any drug (only saline solution was administered); the Ic-3, Ic-10 and Ic-30 bars represent the allodynia percentage calculated for the sensitized animals (injected with capsaicin) and treated with 3, 10 and 30 mg/Kg, respectively, of the Ic compound; and the last bar (Gab) represents the percentage of allodynia obtained for the animals that are sensitized (injected with capsaicin) and treated with 40 mg/Kg of gabapentin. The data are means±SEM (standard error of the mean) of at least 10 animals per experimental group (*** $p<0.001$ ANOVA and Dunnett's test).

Compound Ic showed a notable anti-allodynic effect; this effect was dose-dependent, such that with the highest dose tested, of 30 mg/Kg (bar Ic-30), a reduction of more than 50% of the allodynia was obtained.

Example 2 Effectiveness of the Ic Compound in a Model of Mechanical Allodynia Produced by the Ligation of the Sciatic Nerve For this trial, groups of 6 to 7 mice were used for each group. Mechanical allodynia was induced in the animals (except for the control group) by chronic ligation of the sciatic nerve, and the allodynia induced in this manner was registered 7 days after performing the surgery.

Compound Ic was administered at different doses (3, 30 and 60 mg/Kg) as well as only saline solution as a control, and the positive control gabapentin (40 mg/Kg). The products were administered by stomach tube 45 minutes before performing the allodynia measurement, which was quantified using von Frey filaments, according to the force threshold necessary to cause paw withdrawal of the animal.

The results are summarized in FIG. 2, where the Y-axis represents half of the threshold force that is necessary to apply in order to cause paw withdrawal (50% pain threshold, in grams, g) and the X-axis indicates the different groups and treatments carried out. Thus, from left to right, the first bar represents the control group (Ctrl), in other words, animals without allodynia, meaning, not subjected to surgery and those to which no treatment was administered; the second bar (Ic-0) corresponds to the group of animals with allodynia induced by ligation of the sciatic nerve, but without pharmacological treatment (they were only administered saline solution); the third bar (Gab) corresponds to the animals on which the ligation of the sciatic nerve was performed, and that were treated with gabapentin as a positive control; while the last three bars (Ic-3, Ic-30 and Ic-60) correspond to the animals that were also subjected to ligation of the sciatic nerve and treated with compound Ic, at different doses, of 3, 30 and 60 mg/Kg, respectively. Data points are means±SEM (standard error of the mean) of at least 6 animals per experimental group (' p<0.001 compared to the Ic-0 group; $$$ p<0.001 compared to the Ctrl group; one-way ANOVA followed by Tukey's post-hoc test).

The results represented in FIG. 2 confirm that the administration of the different doses studied of compound Ic is effective for reversing the allodynia induced in the present model. The anti-allodynic effect of the doses of 3 and 30 mg/Kg is notable, while with the higher dose of 60 mg/Kg, apart from producing total reversal of the allodynia, also achieved an analgesic effect.

Figure 3:
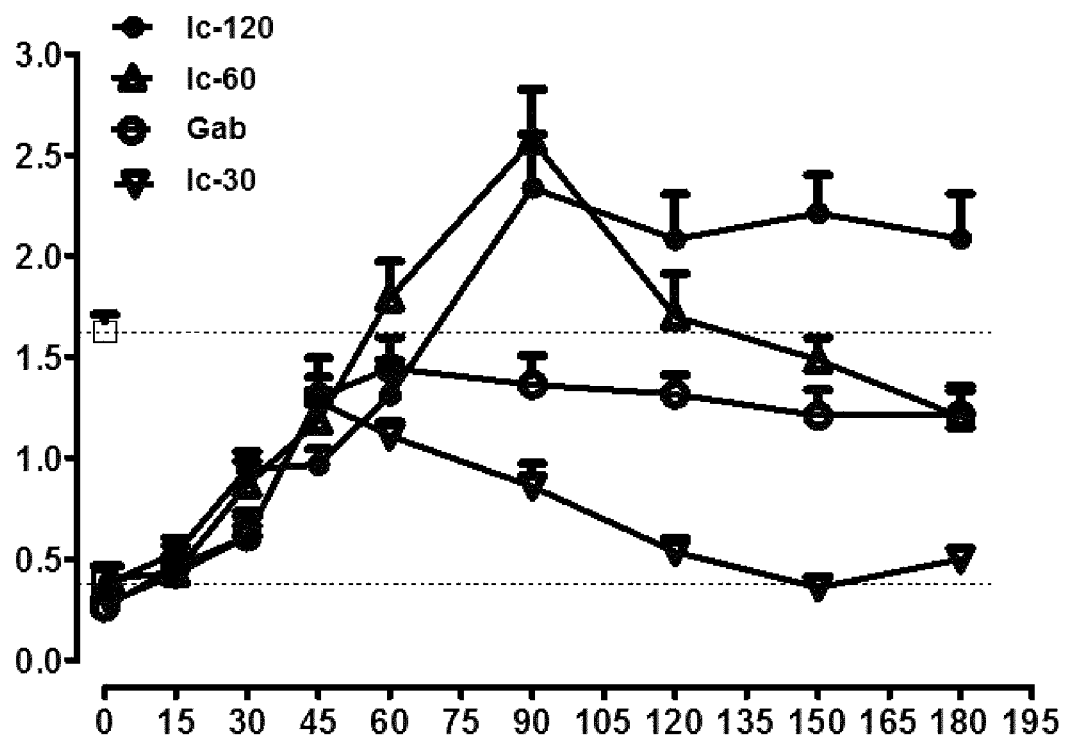
FIG. 3 shows the results obtained with compound Ic orally, administered at different doses, and with gabapentin (Gab) for comparison in the experimental model of mechanical allodynia induced in mice by chronic ligation of the sciatic nerve (Example 2). On the Y-axis half of the threshold force that is necessary to apply in order to cause paw withdrawal is shown (50% pain threshold, in grams, g), while on the X-axis the time elapsed (in minutes) since the administration of each drug is shown. Blank circles represent the animals treated with 40 mg/Kg of gabapentin (positive control), solid circles represent the animals treated with 120 mg/Kg of compound (Ic-120), the triangles represent the animals treated with 60 mg/Kg of compound (Ic-60) and the inverted triangles represent animals treated with 30 mg/Kg of compound (Ic-30). Data points are means±SEM of at least 7 animals per experimental group.

An analogous test was carried out in which several doses of compound Ic (30, 60 and 120 mg/Kg) and gabapentin (40 mg/Kg) were administered, and the 50% pain threshold was measured at different times after the administration in order to evaluate the kinetic of the pharmacological effect and the total duration of the anti-allodynic effect. The results are shown in FIG. 3, where on the Y-axis half of the threshold force that is necessary to apply in order to cause paw's withdrawal is shown (50% pain threshold, in grams, g), while on the X-axis the time elapsed (in minutes) since the administration of each drug is indicated. The blank circles represent the animals treated with gabapentin (positive control), the solid circles represent the animals treated with 120 mg/Kg of compound Ic, the triangles represent the animals treated with 60 mg/Kg of compound Ic and the inverted triangles represent the animals treated with a dose of 30 mg/Kg of compound Ic. Data points are means±SEM (standard error of the mean) of at least 7 animals per experimental group.

Example 3 Effectiveness of the Ic Compound in a Model of Neuropathic Pain Induced by Chemotherapy (Paclitaxel)

In this test, groups of mice between 7 and 12 animals were used, to which a daily dose of paclitaxel of 2 mg/Kg was administered by intraperitoneal route for 5 consecutive days (except for the control group). The evaluation of the induced mechanical allodynia was carried out on the $10^{th}$ day after the first paclitaxel injection, and was quantified by using the von Frey filaments, according to the force threshold necessary to cause the paw withdrawal of the animal.

In order to evaluate the capacity of compound Ic in reversing the allodynia induced by paclitaxel, a first baseline measurement was done of the force threshold of the paw withdrawal of the animals, and then a single dose of the compound was administered orally and a new measurement was made 45 minutes after the administration.

Figure 4:
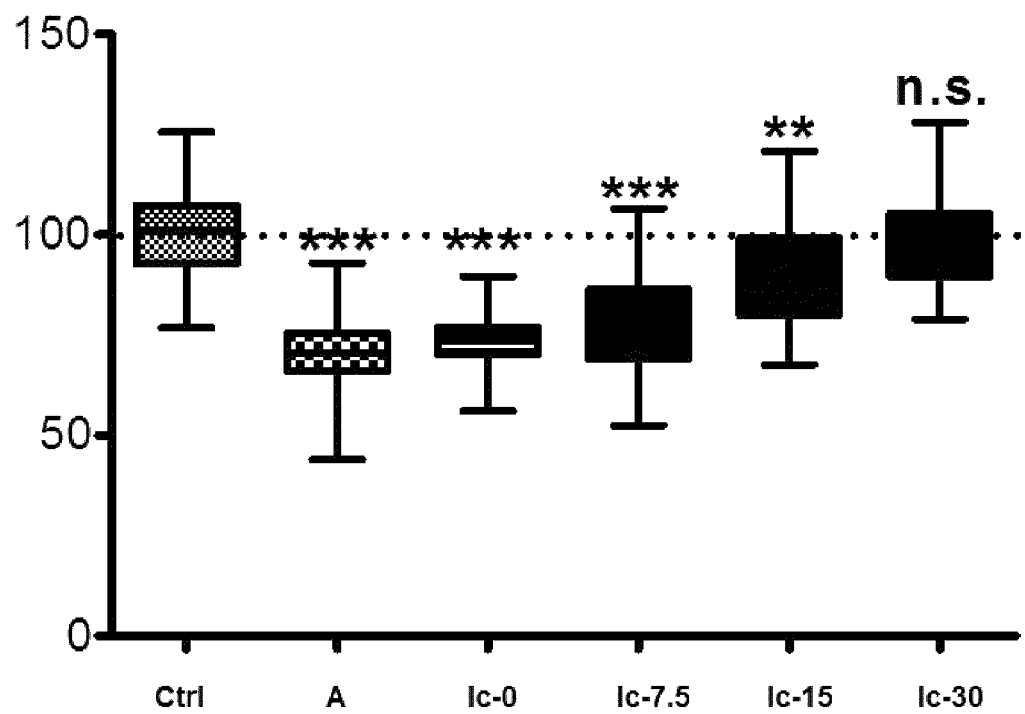
FIG. 4 shows the results obtained with compound Ic in an experimental model of allodynia induced in mice by injecting the chemotherapeutic medication paclitaxel (Example 3). On the Y-axis the threshold force that is necessary to apply in order to cause paw withdrawal of the animals is shown, expressed as a percentage with respect to the control group, made up of animals in which allodynia was not induced; in the X-axis the different groups and treatments performed are represented: Ctrl (control group, without allodynia induction), A (baseline measurement performed on the animals with allodynia induced by paclitaxel, before administering the subsequent treatment), lc-0 (without treatment, only saline solution was administered), Ic-7.5 (animals treated with 7.5 mg/Kg of compound Ic), Ic-15 (animals treated with 15 mg/Kg of compound Ic) and Ic-30 (animals treated with 30 mg/Kg of compound Ic). Data points are means±SEM of at least 7 animals per experimental group (* $p<0.001$,  $p<0.01$; compared to the Ctrl group, one-way ANOVA and post-hoc Dunnett's test).
Figure 5:
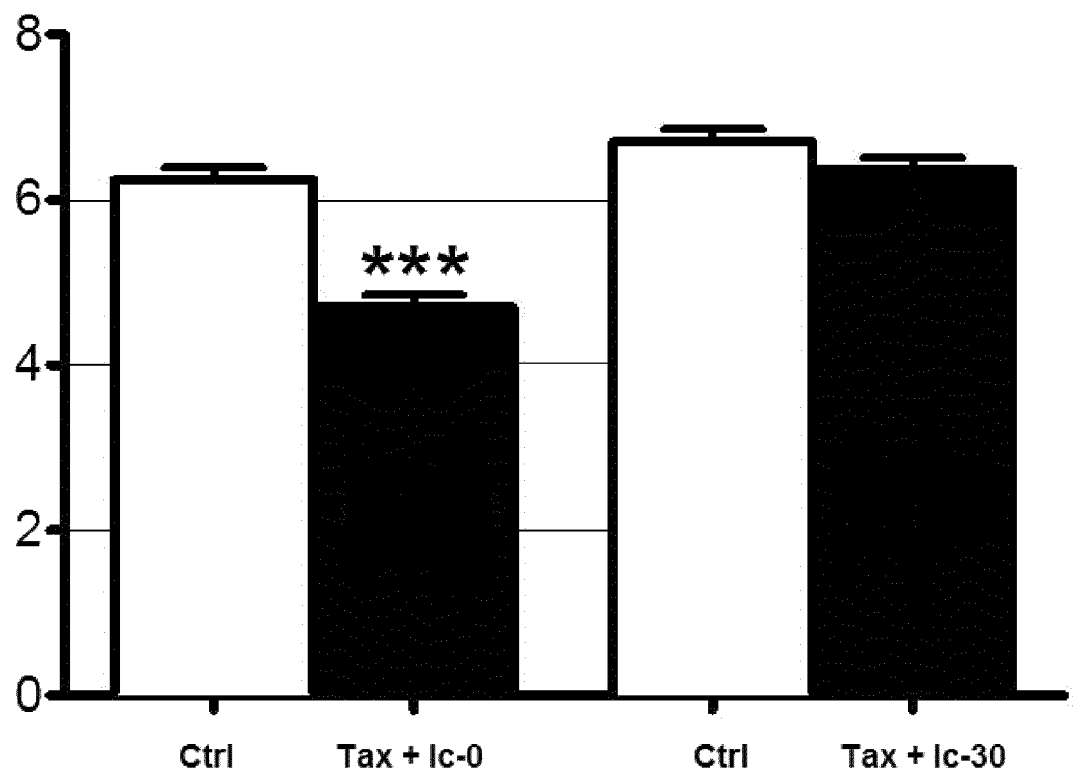
FIG. 5 shows the results obtained with compound Ic in an experimental model of allodynia induced in mice by injecting paclitaxel (Taxol, Tax) (Example 3). A daily dose of Ic was administered for 5 consecutive days, in co-administration with paclitaxel. On the Y-axis the threshold force that is necessary to apply in order to cause paw withdrawal of the animals is shown (in grams, g) and on the X-axis the different groups and treatments are shown. In the first pair of bars the animals without any treatment (Ctrl) are compared to those that received paclitaxel together with saline solution, in other words, they did not receive treatment with compound Ic (Tax+Ic-0). In the second pair of bars the control group (Ctrl) is compared to the group of animals that was treated together with paclitaxel and 30 mg/Kg of compound Ic (Tax+Ic-30). Data points are means±SEM of at least 7 animals per experimental group (*** $p<0.001$, comparison with the Ctrl group, Student's t-test).

The results obtained are represented graphically in FIG. 4, where on the Y-axis the force that is necessary to apply in order to cause paw withdrawal of the animals is shown, expressed as a percentage with respect to the control group, made up of animals in which allodynia was not induced, and on the X-axis the different groups and treatments performed are represented: From left to right, in the first place the control group is represented, without allodynia inducement (Ctrl), and then (A) shows the baseline measurement performed on the animals with allodynia induced by paclitaxel, before administering the treatment, which corresponds to the maximum value of allodynia induced. Below the treatments performed are shown: Ic-0 (without treatment, only saline solution was administered), and Ic-7.5, Ic-15 and Ic-30 which correspond to the administration of 7.5, 15 and 30 mg/Kg of the Ic compound, respectively. Data points are means±SEM (standard error of the mean) of at least 7 animals per experimental group (* p<0.001, p<0.01; compared to the Ctrl group, one-way ANOVA and post-hoc Dunnett's test).

It was observed that the administration of increasing doses of compound Ic reversed the paclitaxel-induced allodynia.

A second trial was carried out using this same model, according to which a daily dose of compound Ic was administered orally, for 5 consecutive days, coadministered with paclitaxel. The allodynia was evaluated the 10th day after the beginning of the treatment.

FIG. 5 shows the results obtained in this trial. On the Y-axis the threshold force that is necessary to apply in order to cause paw withdrawal of the animals is shown (in grams, g), while on the X-axis the different groups and treatments carried out are indicated. In the first pair of bars the animals without any treatment (Ctrl) are compared to those that received paclitaxel together with saline solution, in other words, they did not receive treatment with the Ic compound (Tax+Ic-0). In the second pair of bars the control group (Ctrl) is compared to the group of animals that was treated conjointly with paclitaxel and 30 mg/Kg of the Ic compound (Tax+Ic-30). Data points are means±SEM (standard error of the mean) of at least 7 animals per experimental group (*** p<0.001, comparison with the Ctrl group, Student's t-test).

It was observed that the Ic compound, coadministered with paclitaxel for 5 days prevented the development of allodynia.

Example 4 Effectiveness of Compound Ic in a Model of Cold Allodynia

In this trial 16 mice were used to which 50 µl of a carrageenan solution at 1% were administered by subcutaneous injection in the plantar surface of one of the hind paws. After 3.5 hours since the injection, 60 mg/Kg of the Ic compound was administered orally to 9 of the animals, while only the vehicle (saline solution) was administered to the remaining 7 (control group). The sensitivity to cold was quantified 45 minutes after said treatment by administering a drop of acetone on the plantar surface of the two hind paws, which is, the ipsilateral paw (the same one where the carrageenan was injected) and the contralateral paw (the unsensitized rear paw), and then the time spent licking the paw was measured during a period of 5 minutes after administration of acetone, without taking into account the behavior during the first 15 seconds, since most animals have an initial reaction time to the application.

The results of the trial are shown in FIG. 6, where on the Y-axis the time spent licking the paw (in seconds) is represented and on the X-axis the different groups and treatments are represented. The first pair of bars corresponds to the control group of animals and the second pair of bars corresponds to the animals treated with 60 mg/Kg of compound Ic. In both cases, the bar on the left (striped) represents the results for the sensitized hind paw (ipsilateral) and the right bar (empty) represents the results for the other hind paw, unsensitized (contralateral). In all cases, the data points are means±SEM (standard error of the mean) for the 7 or 9 animals, respectively, of each group (**p<0.01 compared to white bar of the Ctrl, two-way unpaired t-test; ###p<0.001 compared to the gray bar of the Ctrl, two-way unpaired t-test).

A strong cold allodynia effect was observed in the hind paw of the animals sensitized by carrageenan (ipsilateral), while this effect was completely reversed in the animals treated with the Ic compound, as can be seen in the graph upon comparing the results for the ipsilateral paw (striped bars) between the control animals (Ctrl) and the animals treated with the Ic compound (Ic-60).

Example 5 Effectiveness of Compound Ic in a Model of Diabetic Allodynia Induced by Streptozotocin Injection Diabetes was induced in rats by intraperitoneal injection of 60 mg/Kg of streptozotocin for five consecutive days and the evaluation of the allodynia was carried out on day $25^{th}$ after the first injection. Animals were excluded if their plasma glucose value was not higher than 250 mg/ml. For the evaluation of the effect of the Ic compound on the allodynia induced in this manner by diabetes, five groups of animals were used with at least 7 animals in each group, and the allodynia was quantified using von Frey filaments, according to the force threshold necessary to cause the animal's paw's withdrawal.

Compound Ic was administered orally to the animals by gavage, in a single administration and allodynia was measured in each animal immediately before the administration and 45 minutes after the administration. The first group of animals was treated with a dose of 3 mg/Kg of compound Ic, the second group with a dose of 30 mg/Kg of compound Ic and the third, with a dose of 30 mg/kg of the same compound.

The results are summarized in FIG. 7, where on the Y-axis half of the threshold force that is necessary to apply in order to cause the paw's withdrawal is shown (50% pain threshold, in grams, g) and on the X-axis the different groups and treatments are shown in bars. From left to right, the first bar corresponds to the group of animals before starting the experimental protocol, before developing diabetes. Below, the following pair of bars corresponds with the data points obtained in the animals on the $25^{th}$ day after the first streptozotocin injection before, vertical stripes, and after, horizontal stripes, the administration of a saline control solution. Then the following three bars represent the values obtained after the administration of the three different doses of compound Ic; 3, 10 and 30 mg/Kg. Lastly, the white bar represents the values obtained after the administration of the pregabalin compound at 40 mg/kg that acts as a positive control of the experiment. In all the cases, data points are means±SEM (standard error of the mean) for 7-10 animals in each group (p<0.01. *p<0.001 compared to the group of animals administered with saline; gray bar with horizontal stripes. Two-way unpaired t-test). The results represented in FIG. 7 confirm that both doses of compound Ic, 10 and 30 mg/kg, were effective at reversing the allodynia induced in the present model. Especially for the dose of 30 mg/Kg where the differences were statistically significant.

The invention claimed is:

1. A method for the treatment of neuropathic pain comprising administering to a subject in need thereof an effective amount of a compound of formula (I):

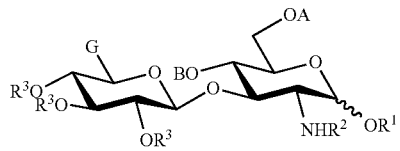

wherein:
   $R^1$ is selected from among hydrogen, linear or branched $C_1$-$C_4$ alkyl, phenylalkyl of less than 10 carbon atoms and —$COCH_3$;
   $R^2$ is selected from among hydrogen, —$COCH_3$ and —$SO_3Y$;
   $R^3$ is selected from among hydrogen, linear or branched $C_1$-$C_4$ alkyl, phenylalkyl of less than 10 carbon atoms, —$COCH_3$ and —COPh, where Ph is phenyl;
   G is selected from among —$COOR^4$ and —COOY;
   one of A or B is selected from among hydrogen, —$SO_3H$, —$SO_3Y$ and —$COCH_3$, and another of A or B is $SO_3H$, or —$SO_3Y$:
   $R^4$ is selected from among hydrogen, $C_1$-$C_2$ alkyl and arylalkyl of less than 16 carbon atoms, and
   Y is an organic or inorganic cation;
or a pharmaceutically acceptable salt or solvate thereof.

2. The method according to claim 1, wherein:
   $R^1$ is selected from among hydrogen and linear $C_1$-$C_4$ alkyl, and
   G is selected from among —$COOR^4$ and —COOY, wherein $R^4$ is hydrogen or $C_1$-$C_2$ alkyl and Y is an inorganic cation.

3. The method according to claim 2, wherein $R^1$ is hydrogen, $R^2$ is —$COCH_3$ and $R^3$ is hydrogen.

4. The method according to claim 2, wherein $R^1$ is methyl, $R^2$ is —$COCH_3$ and $R^3$ is hydrogen.

5. The method according to claim 3, wherein A is hydrogen, B is $SO_3Y$ and G is —COOY, and wherein Y is an inorganic cation.

6. The method according to claim 3, wherein A is —$SO_3Y$, B is hydrogen, and G is —COOY, and wherein Y is an inorganic cation.

7. The method according to claim 3, wherein A and B are —$SO_3Y$ and G is —COOY, and wherein Y is an inorganic cation.

8. The method according to claim 1, wherein the compound of formula (I) is selected from:

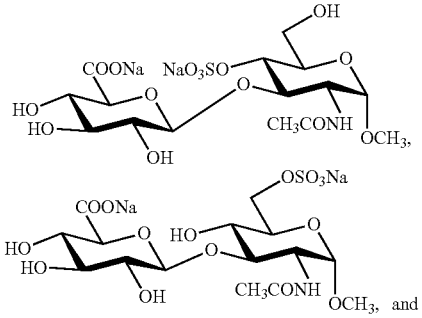

-continued

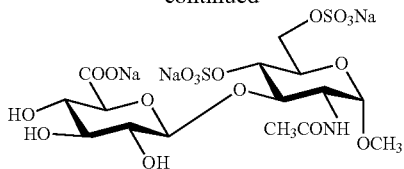

9. The method according to claim 1, wherein the compound of formula (I) is:

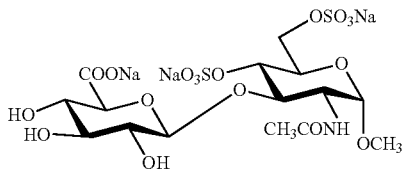

10. The method according to claim 1, wherein the neuropathic pain is selected from: diabetic neuropathy, postherpetic neuralgia, neuropathy induced by chemotherapy, HIV-related neuropathy, rheumatoid arthritis-related neuropathy, osteoarthritis-related neuropathy, fibromyalgia-related neuropathy, trigeminal neuralgia, glossopharyngeal neuralgia, sphenopalatine ganglion neuralgia, vidian nerve neuralgia, persistent idiopathic facial pain, primary atypical facial neuralgia, pain related to phantom limbs, cerebral vascular post-accident pain, post-surgical pain syndrome, pain from multiple sclerosis and pain from spinal cord injuries.

11. The method according to claim 10, wherein the neuropathic pain is selected from: diabetic neuropathy, postherpetic neuralgia, neuropathy induced by chemotherapy and fibromyalgia-related neuropathy.

12. The method according to claim 1, wherein the treatment of the neuropathic pain relates to reversing or preventing the symptoms of mechanical allodynia or cold allodynia.

13. A method for the treatment of neuropathic pain comprising administering to a subject in need thereof an effective amount of a pharmaceutical composition comprising a compound of formula (I), as defined in claim 1, or a pharmaceutically acceptable salt or solvate thereof, and at least one pharmaceutically acceptable excipient.

14. The method according to claim 4, wherein A is hydrogen, B is $SO_3Y$ and G is —COOY, and wherein Y is an inorganic cation.

15. The method according to claim 4, wherein A is —$SO_3Y$, B is hydrogen, and G is —COOY, and wherein Y is an inorganic cation.

16. The method according to claim 4, wherein A and B are —$SO_3Y$ and G is —COOY, and wherein Y is an inorganic cation.

17. The method according to claim 1, wherein the neuropathic pain is selected from:
diabetic neuropathy, postherpetic neuralgia, neuropathy induced by chemotherapy, HIV-related neuropathy, rheumatoid arthritis-related neuropathy, osteoarthritis-related neuropathy, fibromyalgia-related neuropathy, trigeminal neuralgia, glossopharyngeal neuralgia, sphenopalatine ganglion neuralgia, vidian nerve neuralgia, persistent idiopathic facial pain, primary atypical facial neuralgia, pain related to phantom limbs, cerebral vascular post-accident pain, post-surgical pain syndrome and pain from spinal cord injuries.

* * * * *